(12) United States Patent
Kim et al.

(10) Patent No.: US 7,700,617 B2
(45) Date of Patent: *Apr. 20, 2010

(54) SALT OF NAPHTHYRIDINE CARBOXYLIC ACID DERIVATIVE

(75) Inventors: Ae Ri Kim, Daejeon (KR); Jin Hwa Lee, Daejeon (KR); Ki Sook Park, Daejeon (KR); Jong Ryoo Choi, Daejeon (KR); Tae Hee Lee, Daejeon (KR); Jay Hyok Chang, Daejeon (KR); Do Hyun Nam, Daejeon (KR); Hoon Choi, Daejeon (KR)

(73) Assignee: LG Life Sciences, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/635,069

(22) Filed: Dec. 7, 2006

(65) Prior Publication Data

US 2008/0039488 A1 Feb. 14, 2008

Related U.S. Application Data

(63) Continuation of application No. 11/402,048, filed on Apr. 12, 2006, now abandoned, which is a continuation of application No. 10/824,609, filed on Apr. 15, 2004, now abandoned, which is a continuation of application No. 10/223,850, filed on Aug. 20, 2002, now Pat. No. 6,723,734, which is a continuation of application No. 09/923,580, filed on Aug. 6, 2001, now abandoned, which is a continuation of application No. 09/381,491, filed as application No. PCT/KR98/00051 on Mar. 20, 1998, now abandoned.

(30) Foreign Application Priority Data

Mar. 21, 1997 (KR) .................................. 1997/9840

(51) Int. Cl.
*C07D 471/02* (2006.01)
*A61K 31/4745* (2006.01)

(52) U.S. Cl. ...................... 514/300; 546/123
(58) Field of Classification Search ........................ None
See application file for complete search history.

(56) References Cited

U.S. PATENT DOCUMENTS

| | | | |
|---|---|---|---|
| 4,931,446 A | 6/1990 | Berger-Neel et al. |
| 5,286,723 A | 2/1994 | Hayakawa et al. |
| 5,508,428 A | 4/1996 | Hayakawa et al. |
| 5,633,262 A | 5/1997 | Hong et al. |
| 5,698,570 A | 12/1997 | Hong et al. |
| 5,776,944 A | 7/1998 | Hong et al. |
| 5,840,916 A | 11/1998 | Hong et al. |
| 5,869,670 A | 2/1999 | Hong et al. |
| 5,962,468 A | 10/1999 | Hong et al. |
| 6,307,059 B1 | 10/2001 | Chang et al. |

FOREIGN PATENT DOCUMENTS

| | | |
|---|---|---|
| CN | 1114959 A | 1/1996 |
| EP | 0 009 425 A1 | 4/1980 |
| EP | 0 067 666 A1 | 12/1982 |
| EP | 183129 | 6/1986 |
| EP | 266576 | 5/1988 |
| EP | 326891 | 8/1989 |
| EP | 541086 | 5/1993 |
| EP | 0688772 A1 | 12/1995 |
| EP | 787720 | 8/1997 |
| JP | 1-100165 | 4/1989 |
| WO | WO 91/02526 | 3/1991 |
| WO | WO 93/25545 | 12/1993 |
| WO | WO 96/23775 | 8/1996 |
| WO | WO 96/39406 | 12/1996 |
| WO | WO 00/17199 | 3/2000 |

OTHER PUBLICATIONS

Ahn, et al., "Effect of a New Fluoroquinolone LB20304a on Microflora of Caecum of Mice," *Yakhak Hoeji*, 40(3): 343-346 (1996). English translation.

Ahn, Mi-Jeong et al., "Post-Antibiotic Effect of LB20304, A New Quinolone Antibotic," *Yakhak Hoeji*, 1996, 40(3): 347-350. English translation.

Ahn, et al., "In vivo Efficacy of LB20304a against Experimental Respiratory Tract Infection in Mice," *Yakhak Hoeji*, 40(4): 438-441 (1996). English translation.

Biedenbach et al., "Antimicrobial Activity of LB20304 Against Legionella species and Anaerobic Bacteria Using Reference Agar Dilution Methods," *Abstracts of the 37th Interscience Conference on Antimicrobial Agents and Chemotherapy*, Abstract F-170 (1997).

Bouzard et al., "Fluoronaphthyridines as Antibacterial Agents. 4. Synthesis and Structure-Activity Relationships of 5-Substituted-6-fluoro-7-(cycloalkylamino)-1, 4-dihydro-4-oxo-1, 8-naphthyridine-3-carboxylic Acids," *J. Med. Chem.*, 35: 518-525 (1992).

Bryskier, "Update, Anti-infectives, Novelties in the Field of Fluoroquinolones," *Exp. Opin. Invest. Drugs* 6(9): 1227-1245 (1997).

Chu, "Section Review: Anti-infectives, The Future Role of Quinolones," *Exp. Opin. Ther. Patents* 6(8): 711-737 (1996).

Cormican, et al., "Comparative Antimicrobial and Spectrum Activity of LB20304a, a New Fluoronated Naphthyridone Compound," *Abstracts of the 36th ICAAC*, 36: 109, Abstract F53(1996).

(Continued)

*Primary Examiner*—Zinna N Davis
(74) *Attorney, Agent, or Firm*—Finnegan, Henderson, Farabow, Garrett & Dunner, LLP

(57) ABSTRACT

A composition comprising 7-(3-Aminomethyl-4-methoxy-iminopyrrolidin-1-yl)-1-cyclopropyl-6-fluoro-4-oxo-1,4-dihydro-1,8-naphthyridine-3-carboxylic acid methanesulfonate hydrate and their use in antibacterial therapy.

6 Claims, 13 Drawing Sheets

OTHER PUBLICATIONS

Cormican, et al., "Antimicrobial Activity and Spectrum of LB20304, a novel Fluoronaphthyridone," *Antimicrobial Agents and Chemotherapy*, 41(1): 204-211 (1997).

Cooper et al., "Preparation and in Vitro and in Vivo Evaluation of Quinolones with Selective Activity Against Gram-Positive Organisms", J. Med. Chem., 35: 1392-1398 (1992).

Domagala et al., "1-Substituted 7-[3-[(Ethylamino)methyl]-1-pyrrolidinyl]-6,8-difluoro-1,4-dihydro-4-oxo-3-quinolinecarboxylic Acids. New Quantitative Structure-Activity Relationships at $N_1$ for the Quinolone Antibacterials," *J. Med. Chem.*, 31: 991-1001 (1988).

Domagala et al., "Synthesis and Biological Activity of 5-Amino-and 5-Hydroxyquinolones, and the Overwhelming Influence of the Remote $N_1$-Substituent in determining the Structure-Activity Relationship", *J. Med. Chem.*, 34: 1142-1154 (1991).

Garau, "The Role of Quinolones in the Treatment of Community-Acquired Pneumonia," *Medicina Clinica*, 110 (Supp. 1): 31-35 (Feb. 1998). English abstract only.

Hawley's Condensed Chemical Dictionary, twelfth ed., Van Nostrand Reinhold Company: 609 and 1031 (see highlighted portions).

Hohl, et al., "International multicenter investigation of LB20304, a new fluoranaphthyridone," *Clin., Microbiol. Infect.* 4: 280-284 (1998).

Hong, et al., "Novel Fluoroquinolone Antibacterial Agents Containing Oxime-Substituted (Aminomethyl)pyrrolidines: Synthesis and Antibacterial Activity of 7-(4-Aminomethyl)-3-methoxyimino)pyrrolidin-1-y1)-1-cyclopropyl-6-fluoro-4-oxo-1,4-dihydro[1. 8]naphthyridine-3-carboxylic Acid (LB20304)," J. Med. Chem. 40: 3584-3593 (1997).

Kim et al., "Phototoxicity studies of LB20304a," *Korean J. Vet. Pathol.*, 1:40-45 (1997). English translation.

Kim et al., "General Pharmacology of LB20304a, a new Quinolone Antibiotic," *The Journal of Applied Pharmocology*, 4(2): 184-189 (1996). English translation.

Kim et al., "Bacterial Resistance to LB20304, a New Fluoroquinolone Antibiotic," *Arch. Pharm. Res.*, 19(5): 400-405 (1996).

Kim et al., "Novel 6-Methylquinolone Antibacterials: A New Class of Non-6-Fluoroquinolones," *Korean J. of Med. Chem.*, 7(1): 19-22 (1997).

Kim et al., "Safety Evaluation of LB20304, a New Quinolone Antibiotic," *The Journal of Applied Pharmacology*, 3(4): 322-326 (1995).

Kim et al., "Synthesis and Antibacterial Activities of LB20304: A New Fluoronapththyridone Antibiotic Containing Novel Oxime Functionalized Pyrrolidine," *Abstracts of the 35th Interscience Conference on Antimicrobial Agents and Chemotherapy*, Session 122, Abstract F204, 148 (1995).

Kim, Mu-Yong, et al. "In vitro activities of LB20304, a new fluoroquinolone," Arch. Pharmacal Res. (1996), 19(1), pp. 52-59.

Koga et al., "Structure-Activity Relationships of Antibacterial 6,7- and 7,8-Disubstituted 1-Alkyl-1,4-dihydro-4-oixoquinoline-3-carboxylic Acids", *J. Med. Chem.*, 23: 1358-1363 (1980).

Kwak, et al., "Antimicrobial Activities of LB20304a, a New Quinolone Antibiotic," *The Journal of Applied Pharmacology*, 4: 378-384 (1996).

Lesher et al., "1,8-Napththyridine Derivatives. A New Class of Chemotherapeutic Agents", *J. Med Chem.*, 5: 1063-1065 (1962).

Marco, et al., "Antimicrobial Activity of LB20304, a fluoronaphthyridone, tested against anaerobic bacteria," *J. Antimicrob. Chemother.* 40: 605-607 (1997).

Matsumoto et al., "AT-3295, a New Pyridonecarboxylic Acid Derivative with Potent Antibacterial Activity: Synthesis and Structure-activity Relationships", *Proceedings of the 14th International Congress of Chemotherapy*, 1519-1520 (1985).

Nam et al., "New Quinolone Antibacterial Agents Introducing New Functional Groups at C-3 Position," *Korean J. Med. Chem.*, 6(2): 203-238 (1996).

Oh et al., "In vitro and In vivo Antibacterial Activities of LB20304, a New fluoronapththyridone," *Abstracts of the 35th Interscience Conference on Antimicrobial Agents and Chemotherapy*, Session 122, Abstract F205, 148 (1995).

Oh, Jeong-In, et al. "In vitro and in vivo evaluations of LB20304, a new fluoronaphthyridone," Antimicrob Agents Chemother. (1996), 40(6), pp. 1564-1568.

Paek, Kyoung-Sook, et al. "Factors affecting in vitro activity of LB20304, a new fluoroquinolone," Arch. Pharm. Res., 1996, 19(2), 143-147.

Paek, Kyoung-Sook, et al. "Bactericidal activities of LB20304, a new fluoroquinolone," Arch. Pharmacal Res. (1996), 19(4), pp. 317-320.

Parikh and von E. Doering, "Sulfur Trioxide in the Oxidation of Alcohols by Dimethyl Sulfoxide", *JACS*, 89: 5505-5507 (1967).

Rosen et al., "Design, Synthesis, and Properties of (4S)-7-(4-Amino-2-substituted-pyrrolidin-1-yl) quinolone-3-carboxylic Acids", *J. Med. Chem.*, 31: 1598-1611 (1988).

Sato et al., "In Vitro and In Vivo Activity of DL-8280, a New Oxazine Derivative", *Antimicrob. Agents Chemother.*, 22: 548-553 (1982).

Seo, et al., "High Performance Liquid Chromatographic Assay of a New Fluoroquinolone, LB20304, in the Plasma of Rats and Dogs," *Arch. Pharm. Res.*, 19(6): 554-558 (1996).

Seo, et al., "Pharmacokinetics of LB20304, a New Fluoroquinolone, in Rats and Dogs," Arch. Pharm. Res., 19(5): 359-367 (1996).

Seo, et al., "Pharmacokinetics of a New Quinolone LB20304a, In Rats and Dogs," *Annual Meeting of the American Association of Pharmaceutical Scientists Seattle*, 13(9): S-486, Abstract PPDM 8374 (1996).

Sharma et al., "Fluoroquinolones: Antimicrobial Agents of the 90's," *Indian Journal of Pharmacology*, 26: 249-261 (1994).

Stedman's Medical Dictionary, 26th ed., Williams & Wilkins: 814 and 1604 (see highlighted portions).

The Oxford Dictionary for Scientific Writers and Editors, Clarendon Press: 179 and 312 (see highlighted portions).

Wise et al., "Inv Vitro Activity of Bay 09867, A New Quinoline Derivative, Compared with Those of Other Antimicrobial Agents", *Antimicrob. Agents Chemother.*, 23: 559-564 (1983).

CA 114: 164195r, 775 (1991).

CA 119: 203318h, 884 (1993).

Byrn et al., "Solid State Pharmaceutical Chemistry", Chem. Mater. vol. 6, pp. 1146-58 (1994).

Byrn et al., "Pharmaceutical Solids: A Strategic Approach to Regulatory Considerations," Pharmaceutical Research vol. 12., No. 7, pp. 945-54 (1995).

Hilfiker et al., "Relevance of Solid-state Properties for Pharmaceutical Products," in Polymorphism: in the Pharmaceutical Industry, Ed. R. Hilfiker, pp. 1-19 Wiley-VCH verlag GmbH & Co. KGaA (2006).

Morris et al., "An Integrated Approach to the Selection of Optimal Salt Form for a New Drug Candidate," International Journal of Pharmaceutics, vol. 105, pp. 209-17 (1994).

Arthur Vogel, Section 1.20 "Teoria da Ação de Agentes Desecantes, pp. 43-47 " in Quimica Orgânica - Anáalise Orgánica Qualitative (Qualitiative Organic Chemistry) vol. 1 (1990).

SALT OF NAPHTHYRIDINE CARBOXYLIC ACID DERIVATIVE

This is a continuation of application Ser. No. 11/402,048, filed Apr. 12, 2006, now abandoned which is a continuation of application Ser. No. 10/824,609, filed Apr. 15, 2004, now abandoned which is a continuation of application Ser. No. 10/223,850, filed Aug. 20, 2002, issued as U.S. Pat. No. 6,723,734 on Apr. 20, 2004, which is a continuation of application Ser. No. 09/923,580, filed Aug. 6, 2001, abandoned, which is a continuation of application Ser. No. 09/381,491, filed Dec. 8, 1999, abandoned, which is a section 371 U.S. national stage application of PCT/KR98/00051, filed Mar. 20, 1998, and claims the benefit under 35 U.S.C. § 119 of Republic of Korea Application No. 1997/9840, filed Mar. 21, 1997, all of which are incorporated by reference.

TECHNICAL FIELD

The present invention relates to a salt and associated hydrates of racemic 7-(3-aminomethyl-4-methoxyiminopyrrolidin-1-yl)-1-cyclopropyl-6-fluoro-4-oxo-1,4-dihydro-1,8-naphthyridine-3-carboxylic acid, processes for their preparation, pharmaceutical compositions comprising them, and their use in antibacterial therapy.

BACKGROUND ART

EP 688772 (corresponding to Korean Patent Laid open Publication No 96-874) discloses novel quinoline(naphthyridine)carboxylic acid derivatives, including anhydrous 7-(3-aminomethyl-4-methoxyiminopyrrolidin-1-yl)-1-cyclopropyl-6-fluoro-4-oxo-1,4-dihydro-1,8-naphthyridine-3-carboxylic acid of formula I, having antibacterial activity.

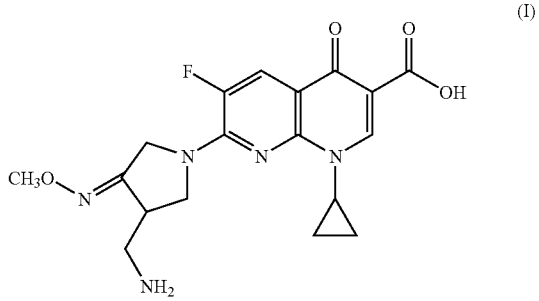

(I)

DISCLOSURE OF INVENTION

According to the invention there is provided 7-3-Aminomethyl-4-methoxyiminopyrrolidin-1-yl)-1-cyclopropyl-6-fluoro-4-oxo-1,4-dihydro-1,8-naph-thyridine-3-carboxylic acid methanesulfonate.

7-(3-Aminomethyl-4-methoxyiminopyrrolidin-1-yl)-1-cyclopropyl-6-fluoro-4-oxo-1,4-dihydro-1,8-naphthyridine-3-carboxylic acid methanesulfonate (hereinafter referred to as 'the methanesulfonate') may be obtained as an anhydrate or a hydrate i.e. methanesulfonate.$nH_2O$.

Hydrates of the methanesulfonate wherein n is in the range 1 to 4 are preferred. Particular hydrates of the methanesulfonate which may be mentioned are those in which n is 1, 1.5, 2, 2.5, 3, 3.5 and 4. Particularly preferred compounds are those in which n is 1.5 or 3, with n=1.5 being most preferred.

The moisture content of the methanesulfonate hydrates varies with the hydration number (n) of the hydrated molecule. The methanesulfonate has a molecular weight of 485.5 thus the calculated moisture content of hydrates where n is 1, 1.5, 2, 2.5, 3, 3.5 and 4 is 3.6%, 5.0%, 6.9%, 8.5%, 10.0%, 11.5% and 12.9% respectively. However, the actual moisture content of the methanesulfonate hydrates may differ from the calculated value depending on various factors including recrystallization conditions and drying conditions. The observed moisture content for the methanesulfonate hydrates where n is 1, 1.5, 2, 2.5, 3, 3.5 and 4 is shown in Table 1:

TABLE 1

| Hydration Number (n) | Moisture Content (% w/w) |
|---|---|
| 1 | 2~4 |
| 1.5 | 4~6 |
| 2 | 6~8 |
| 2.5 | 8~9 |
| 3 | 9~11 |
| 3.5 | 11~12 |
| 4 | 12~13 |

It is possible to mix methanesulfonate hydrates having different moisture contents together to give materials having intermediate moisture contents.

Preferred methanesulfonate hydrates have a moisture content of from 4 to 6% or from 9 to 11%, especially a moisture content of from 4 to 6%.

The methanesulfonate has been observed to exist as a stable hydrate over a range of hydration numbers (n). Stability of the hydrate refers to its resistance to loss or gain of water molecules contained in the compound. The methanesulfonate hydrates maintain a constant moisture content over an extended relative humidity range. The n=3 hydrate has a constant moisture content at a relative humidity of from at least 23 to 75%, and the n=1.5 hydrate has a constant moisture content at a relative humidity of from 23 to 64% (see FIGS. 3 and 4). In contrast, moisture absorption by the anhydrate varies greatly with relative humidity.

Both the methanesulfonate anhydrate and n=3 hydrate undergo transition to the n=1.5 hydrate in aqueous suspension indicating that the latter is thermodynamically more stable. The n=1.5 hydrate is a sesquihydrate at 11 to 64% of relative humidity. Above 75% relative humidity, it takes up water over 10% and its X-ray diffraction pattern changes. The hydrate (another form of n=3 having different physiochemical properties from the n=3 hydrate of Example 2) obtained from n=1.5 hydrate at 93% relative humidity is not stable at lower relative humidity, it converts back to n=1.5 hydrate at a relative humidity below 75%.

Since the moisture content of the anhydrate changes readily depending on the environment e.g. relative humidity, formulation additives etc, it may require careful handling during storage or formulation, with operations such as quantifying procedures being performed in a dry room. The hydrates do not change in moisture content as easily and hence products which are stable to prolonged storage and formulation may be obtained. The hydrate can be tabletted without the addition of a binder since the water contained in the compound itself acts a binder, whereas it may not be possible to tablet the anhydrate at a similar pressure.

The present invention also provides a process for the preparation of 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate and hydrates thereof which comprises reacting 7-(3-aminomethyl-4-methoxyiminopyrrolidin-1-yl)-1-cyclopropyl-6-fluoro-4-oxo-1, 4-dihydro-1,8-naphthyridine-3-carboxylic acid with methanesulfonic acid and crystallizing the resulting methanesulfonate from solution, and where desired or necessary adjusting the hydration of the compound.

The methanesulfonate and its hydrates may be prepared by the addition of methanesulfonic acid to the free base which may be prepared as described in EP 688772. Preferably, 0.95 to 1.5 molar equivalents of methanesulfonic acid is added to the free base, or 1 molar equivalent of methanesulfonic acid dissolved in a suitable solvent is added to the free base. Suitable solvents for the preparation of the methanesulfonate and its hydrates include any solvent in which the methanesulfonate is substantially insoluble, suitable solvents include $C_1$-$C_4$ haloalkanes, $C_1$-$C_8$ alcohols and water, or mixtures thereof. Dichloromethane, chloroform, 1,2-dichloroethane, methanol, ethanol, propanol and water, or mixtures thereof, are preferred solvents. If necessary, the free base may be heated in the solvent to facilitate solution before methanesulfonic acid is added, alternatively the methanesulfonic acid may be added to a suspension, or partial suspension, of the free base in the solvent. Following addition of the methanesulfonic acid the reaction mixture is preferably allowed to stand or is stirred for 1 to 24 hours at a temperature of from about −10 to 40° C. The resulting methanesulfonate is obtained as a solid which can be isolated by filtration or by removal of the solvent under reduced pressure.

Different hydrates may be obtained by altering the recrystallization conditions used in the preparation of the methanesulfonate, such conditions may be ascertained by conventional methods known to those skilled in the art.

The present invention also provides a process for the preparation of a hydrate of 7-(3-aminomethyl-4-methoxyiminopyrrolidin-1-yl)-1-cyclopropyl-6-fluoro-4-oxo-1,4-dihydro-1, 8-naphthyridine-3-carboxylic acid methanesulfonate comprising exposing the methanesulfonate anhydrate or a solvate thereof to a high relative humidity.

The methanesulfonate anhydrate or solvate thereof is preferably exposed to a relative humidity of at least 75%.

The methanesulfonate anhydrate or solvate thereof may be exposed to high relative humidity by passing humidified nitrogen gas through the methanesulfonate anhydrate or solvate thereof or by standing the methanesulfonate anhydrate or solvates thereof under a high relative humidity.

The humidified nitrogen gas used in this process, for example nitrogen gas having a humidity of at least 75%, may be made by conventional methods. In this process it is desirable to maintain the temperature in the range above which moisture condensation could occur. Also, particularly in large scale production, it is preferable to stir the sample thoroughly while the humidified nitrogen gas is passed through. When the hydrate is prepared by standing the methanesulfonate anhydrate or solvate thereof under a high relative humidity, for example a relative humidity of at least 75%, it is preferable to spread the sample as thinly as possible in order to raise the conversion efficiency.

The solvates of methanesulfonate anhydrate which may be used in the process according to this aspect of the present invention include solvates with one or more organic solvents. Preferred solvents include $C_1$-$C_4$ haloalkanes and $C_1$-$C_8$ alcohols, for example those selected from the group consisting of ethanol, dichloromethane, isopropanol and 2-methyl-2-propanol.

Solvates of the methanesulfonate anhydrate are novel. Thus according to a further aspect of the invention there is provided a solvate of 7-(3-aminomethyl-4-methoxyiminopyrrolidin-1-yl)-1-cyclopropyl-6-fluoro-4-oxo-1,4-dihydro-1, 8-naphthyridine-3-carboxylic acid methanesulfonate with one or more organic solvents.

The solvates of the methanesulfonate are prepared by recrystallization and controlled by the condition of recrystallizing system.

The methanesulfonate and its hydrates exhibit the same potent antibacterial activity as the corresponding free base disclosed in EP 688772. The methanesulfonate and its hydrates also exhibit desirable physicochemical properties including improved solubility and constant moisture content regardless of the ambient relative humidity when compared to the free base and other salts thereof. The methanesulfonate and its hydrates thus exhibit greater ease of handling, quality control and formulation than the free base and other salts thereof.

As mentioned above the methanesulfonate and its hydrates exhibit antibacterial activity. The methanesulfonate and its hydrates may be formulated for administration in any convenient way for use in human or veterinary medicine, according to techniques and procedures per se known in the art with reference to other antibiotics, and the invention therefore includes within its scope a pharmaceutical composition comprising 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate or a hydrate thereof together with a pharmaceutically acceptable carrier or excipient.

Compositions comprising the methanesulfonate or hydrate thereof as active ingredient may be formulated for administration by any suitable route, such as oral, parenteral or topical application. The compositions may be in the form of tablets, capsules, powders, granules, lozenges, creams or liquid preparations, such as oral or sterile parenteral solutions or suspensions. Tablets and capsules for oral administration may be in unit dose presentation form and may contain conventional excipients such as binding agents, for example, hydroxypropyl methyl cellulose, hydroxy propyl celullose, syrup acacia, gelatin, sorbitol, tragacanth, or polyvinylpyrrollidone; fillers, for example microcrystalline cellulose, lactose, sugar, maize-starch, calcium phosphate, sorbitol or glycine; tabletting lubricants, for example magnesium stearate, talc, polyethylene glycol or silica; disintegrants, for example sodium starch glycolate, cross linked polyvinyl pyrollidone or potato starch; or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethyl cellulose, caboxymethyl cellulose, aluminium stearate gel or hydrogenated edible fats; emulsifying agents, for example lecithin, sorbitan monooleate, or acacia; non-aqueous vehicles (which may include edible oils), for example almond oil, oily esters, glycerine, propylene glycol, or ethyl alcohol; preservatives, for example methyl or propyl p-hydroxybenzoate or sorbic acid; and, if desired conventional flavouring or coloring agents. Suppositories will contain conventional suppository base, e.g. cocoa-butter or other glyceride.

For parenteral administration, fluid unit dosage forms are prepared utilising the compound and a sterile vehicle, water being preferred. The methanesulfonate or hydrate thereof, can be either suspended or dissolved in the vehicle, depending on the vehicle and concentration used. In preparing solutions the methanesulfonate or hydrate thereof can be dissolved in water for injection and filter sterilized before filling into a suitable vial or ampoule and sealing. Advantageously, agents such as local anaesthetic, preservative and buffering agents can be dissolved in the vehicle. To enhance the stability, the composition can be lyophilised and the dry lyophilised powder sealed in a vial, an accompanying vial of water for injection may be supplied to reconstitute the powder prior to use. Parenteral suspensions are prepared in substantially the same manner except that the methanesulfonate or hydrate thereof is suspended in the vehicle instead of being dissolved and sterilization cannot be accomplished by filtration. The methansulfonate or hydrate thereof can be sterilized by exposure to ethylene oxide before suspending in the sterile vehicle. Advantageously, a surfactant or wetting agent is included in the composition to facilitate uniform distribution of the methanesulfonate or hydrate thereof.

The methanesulfonate or hydrate thereof may also be formulated as an intramammary composition for veterinary use.

The composition may contain from 0.1% to 100% by weight, preferably from 10 to 99.5% by weight, more preferably from 50 to 99.5% by weight of the active ingredient measured as the free base, depending on the method of administration. Where the compositions comprise dosage units, each unit will preferably contain from 50-1500 mg of the active ingredient measured as the free base. The dosage as employed for adult human treatment will preferably range from 100 mg to 12 g per day for an average adult patient (body weight 70 kg), for instance 1500 mg per day, depending on the route and frequency of administration. Such dosages correspond to approximately 1.5 to 170 mg/kg per day. Suitably the dosage is from 1 to 6 g per day.

The daily dosage is suitably given by administering the active ingredient once or several times in a 24-hour period, e.g. up to 400 mg maybe adminstered once a day, in practice, the dosage and frequency of administration which will be most suitable for an individual patient will vary with the age, weight and response of the patients, and there will be occasions when the physician will choose a higher or lower dosage and a different frequency of administration. Such dosage regimens are within the scope of this invention.

The present invention also includes a method of treating bacterial infections in humans and animals which method comprises administering a therapeutically effective amount of 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate or a hydrate thereof.

In a further aspect, the present invention also provides the use of 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate or a hydrate thereof for the manufacture of a medicament for treating bacterial infection.

The methanesulfonate and its hydrates are active against a broad range of Gram-positive and Gram-negative bacteria, and may be used to treat a wide range of bacterial infections including those in immunocompromised patients.

Amongst many other uses, the methanesulfonate and its hydrates are of value in the treatment of skin, soft tissue, respiratory tract and urinary tract infections, and sexually transmitted diseases in humans. The methanesulfonate and its hydrates may also be used in the treatment of bacterial infections in animals, such as mastitis in cattle.

BRIEF DESCRIPTION OF DRAWINGS

The following examples and figures illustrate the invention but are not intended to limit the scope in any way.

FIG. 8 shows the variation in moisture content with elapsed time of the methanesulfonate anhydrate of Example 1, taken after 0, 5, 10, 20, 30, and 60. minutes, respectively, from the initial point of passing humidified nitrogen gas through;

FIG. 11 shows the change in X-ray diffraction pattern with elapsed time of the methanesulfonate solvate (ethanol content 0.11%) of Example 4, from initial point of passing the humidified nitrogen gas having a relative humidity of 93% through.

BEST MODE FOR CARRYING OUT THE INVENTION

The present inventors have performed several experiments in order to identify the moisture content and physicochemical property of the methanesulfonate anhydrate and each hydrate, and the results are described in connection with the drawings in the following.

Figure 1:
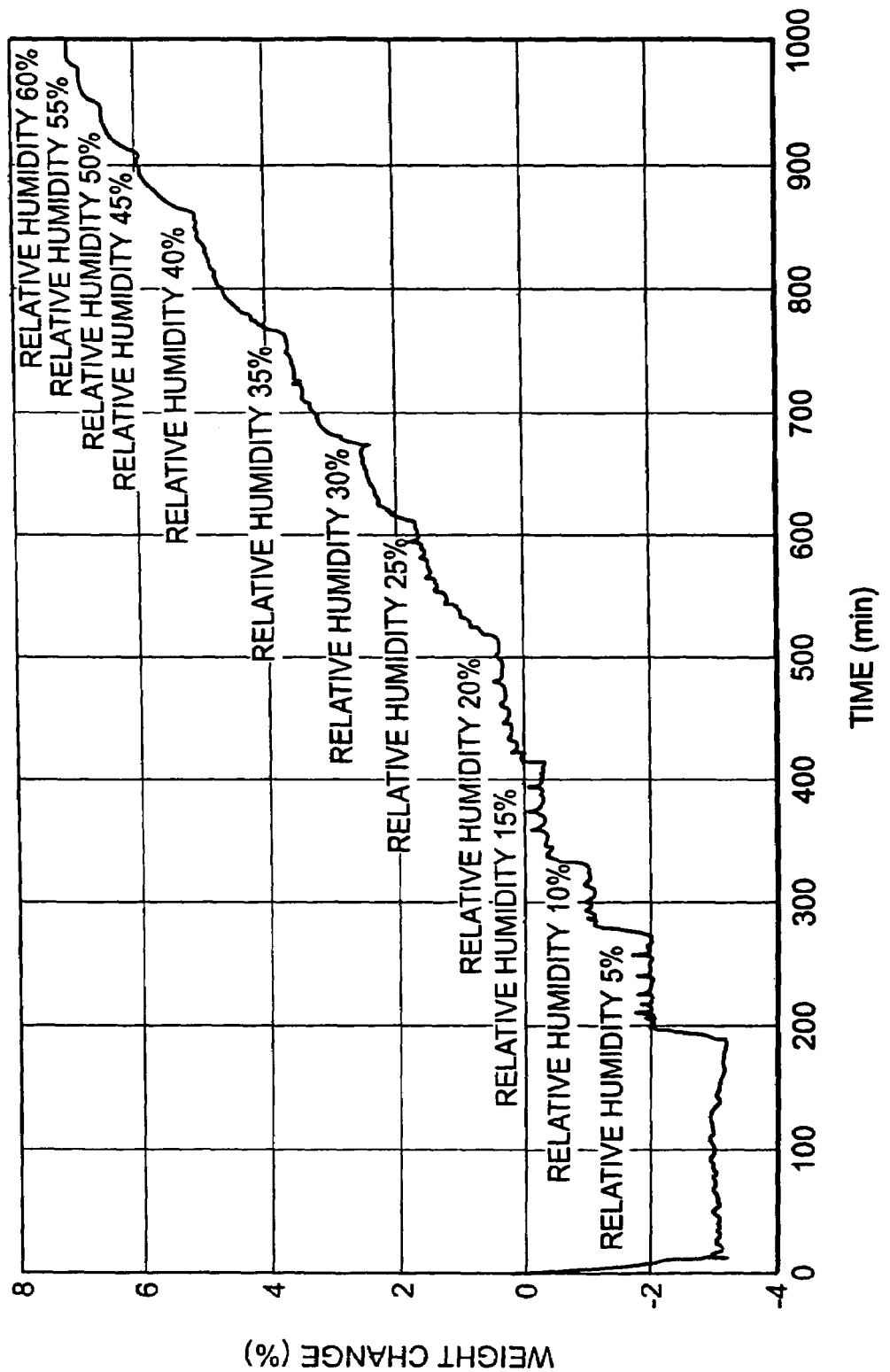
FIG. 1 shows the moisture sorption profile of methanesulfonate anhydrate of Example 1 at 25° C. at several relative humidities.
Figure 2:
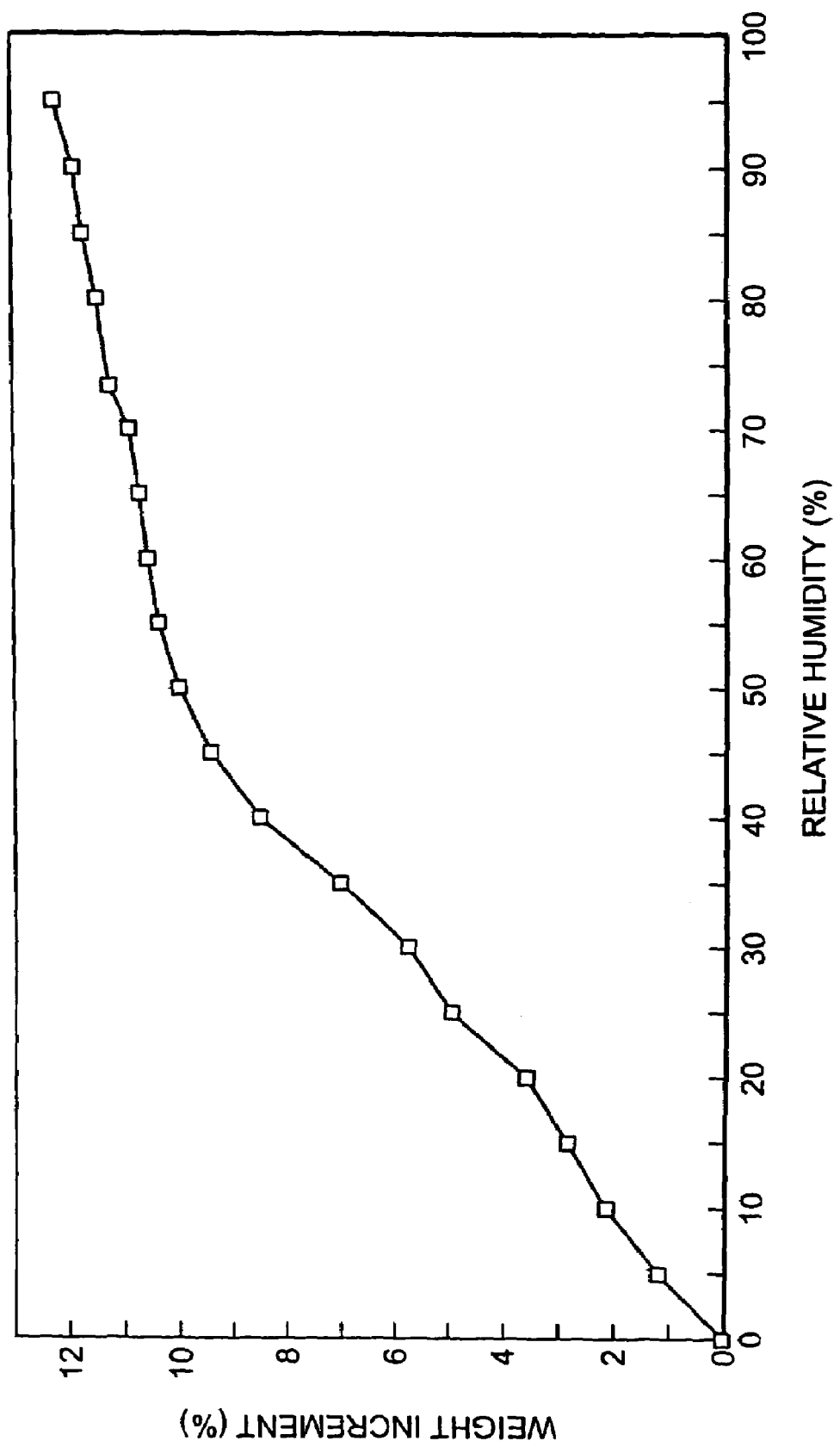
FIG. 2 shows the isothermal moisture sorption profile of methanesulfonate anhydrate of Example 1 at 25° C.
Figure 3:
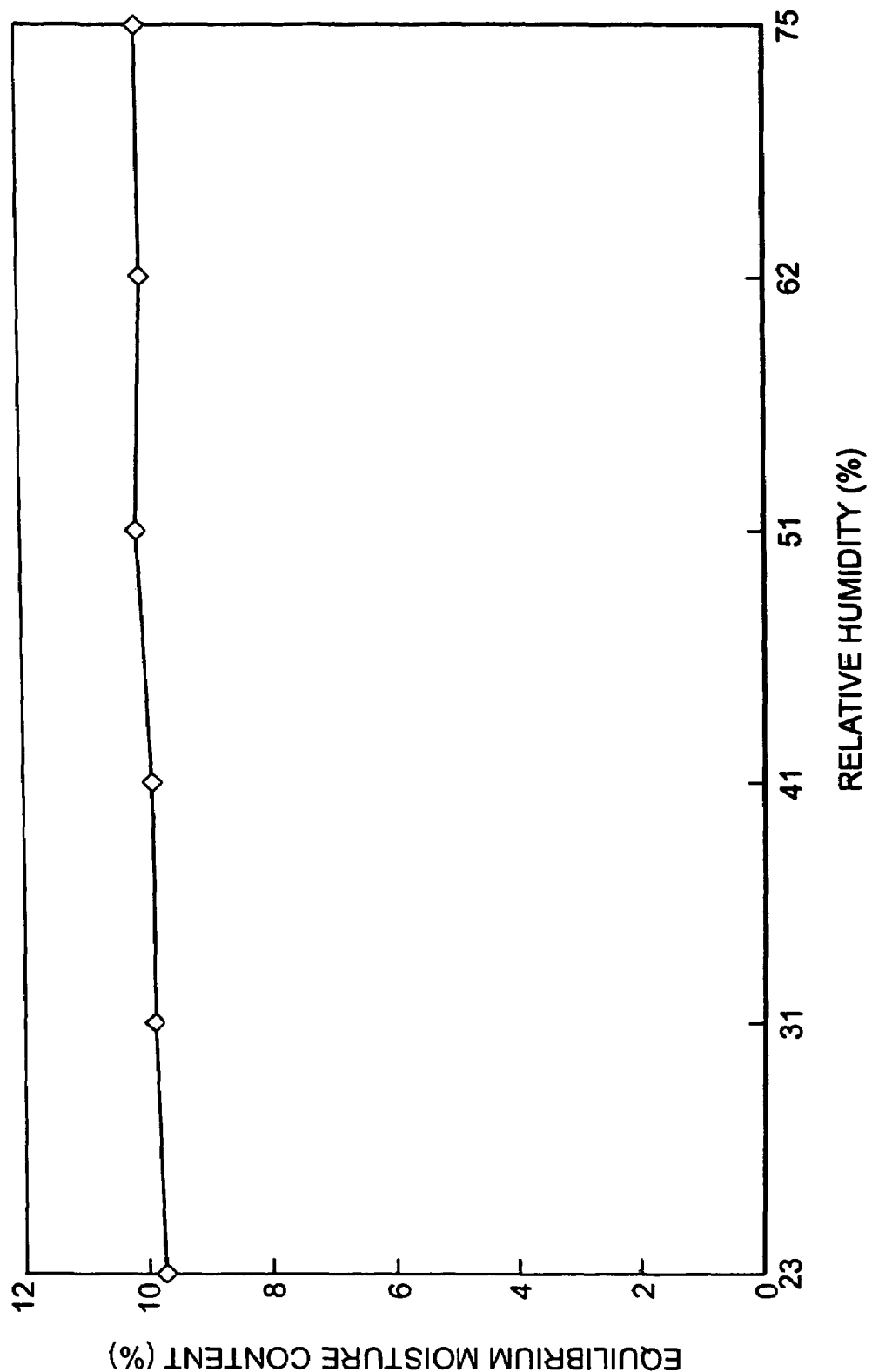
FIG. 3 shows the equilibrium moisture content of the methanesulfonate n=3 hydrate of Example 2 at a relative humidity of 23 to 75%.
Figure 4:
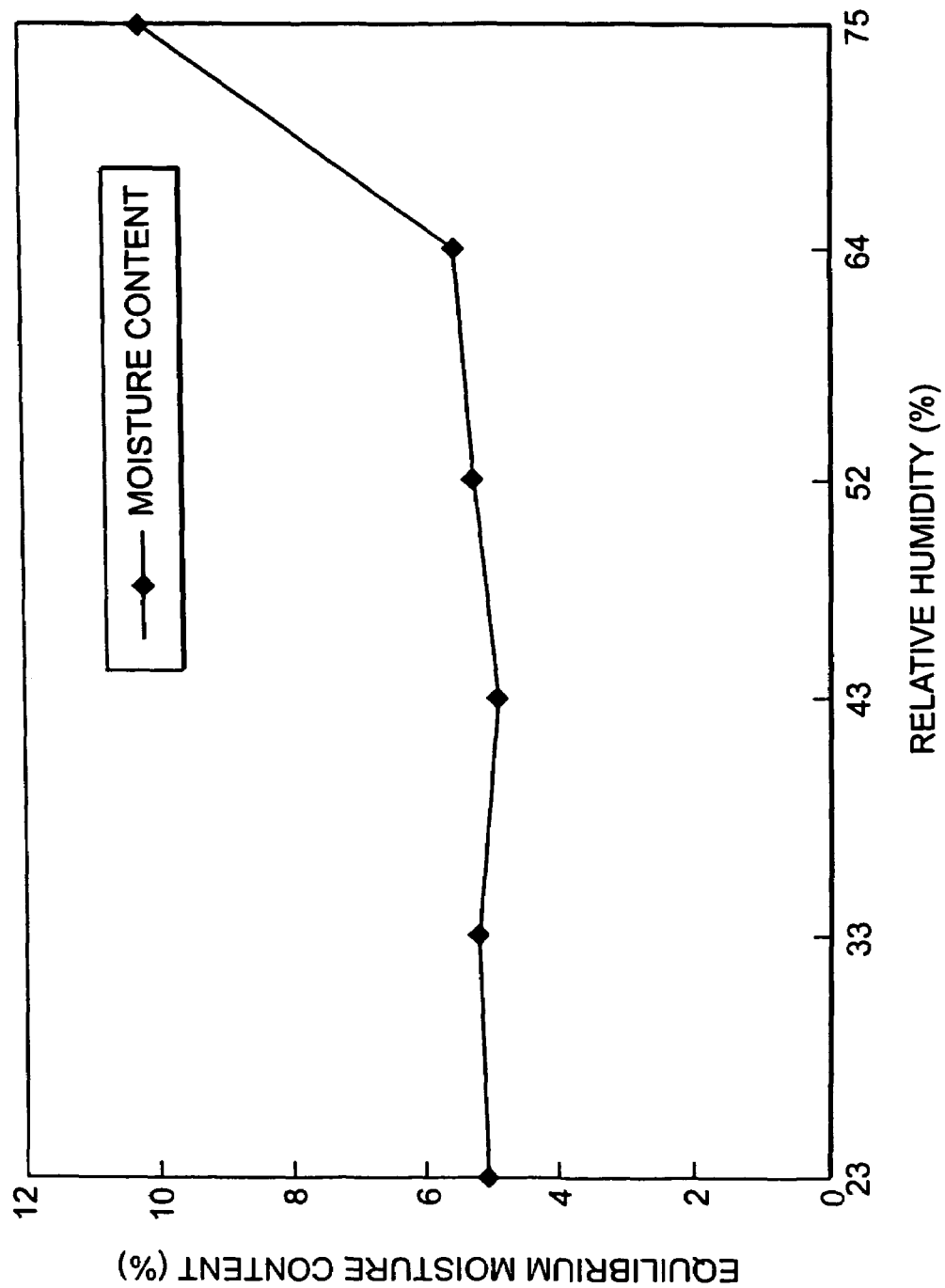
FIG. 4 shows the equilibrium moisture content of the methanesulfonate n=1.5 hydrate of Example 3 at a relative humidity of 23 to 75%.

FIG. 1 shows the moisture sorption velocity profile of 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate anhydrate at several relative humidities. Over the whole range of relative humidity tested, the initial moisture adsorption proceeds rapidly at each relative humidity. In most cases equilibrium is achieved within 2 hours. FIG. 2 shows the isothermal moisture sorption profile of the methanesulfonate anhydrate according to the change in relative humidity at 25° C. The weight increment (%) of Y-axis represents the equilibrium moisture content, from which it can be recognized that the equilibrium moisture content depends on the relative humidity. FIG. 3 shows the equilibrium moisture content of the n=3 hydrate (which is obtained by recrystallization from a solvent mixture of ethanol and water) after it is allowed to stand for 2 weeks under relative humidities in the range of 23 to 75%. The result shows that the n=3 hydrate is more stable than the anhydrate since it maintains a moisture content of around 10% under the relative humidities tested. FIG. 4 shows the isothermal moisture adsorption profile of the n=1.5 hydrate. Here, it maintains a moisture content of around 5% under the relative humidity in the range of 23 to 64%. Thus, it is also identified as a stable hydrate.

It has been identified that the physical properties of the hydrate are very different from those of the anhydrate.

Figure 5:
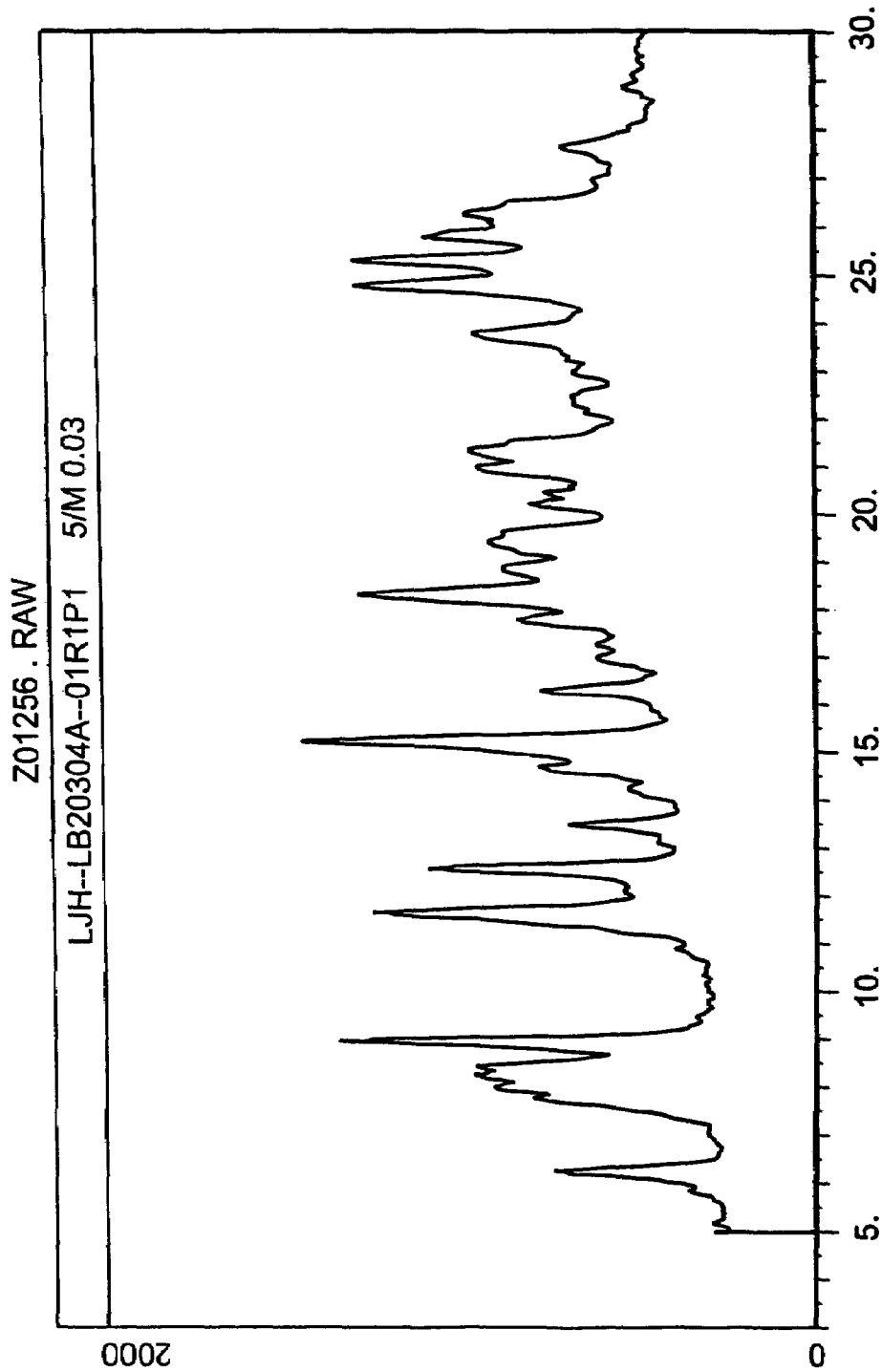
FIG. 5 shows the powder X-ray diffraction pattern of the methanesulfonate anhydrate of Example 1.
Figure 6:
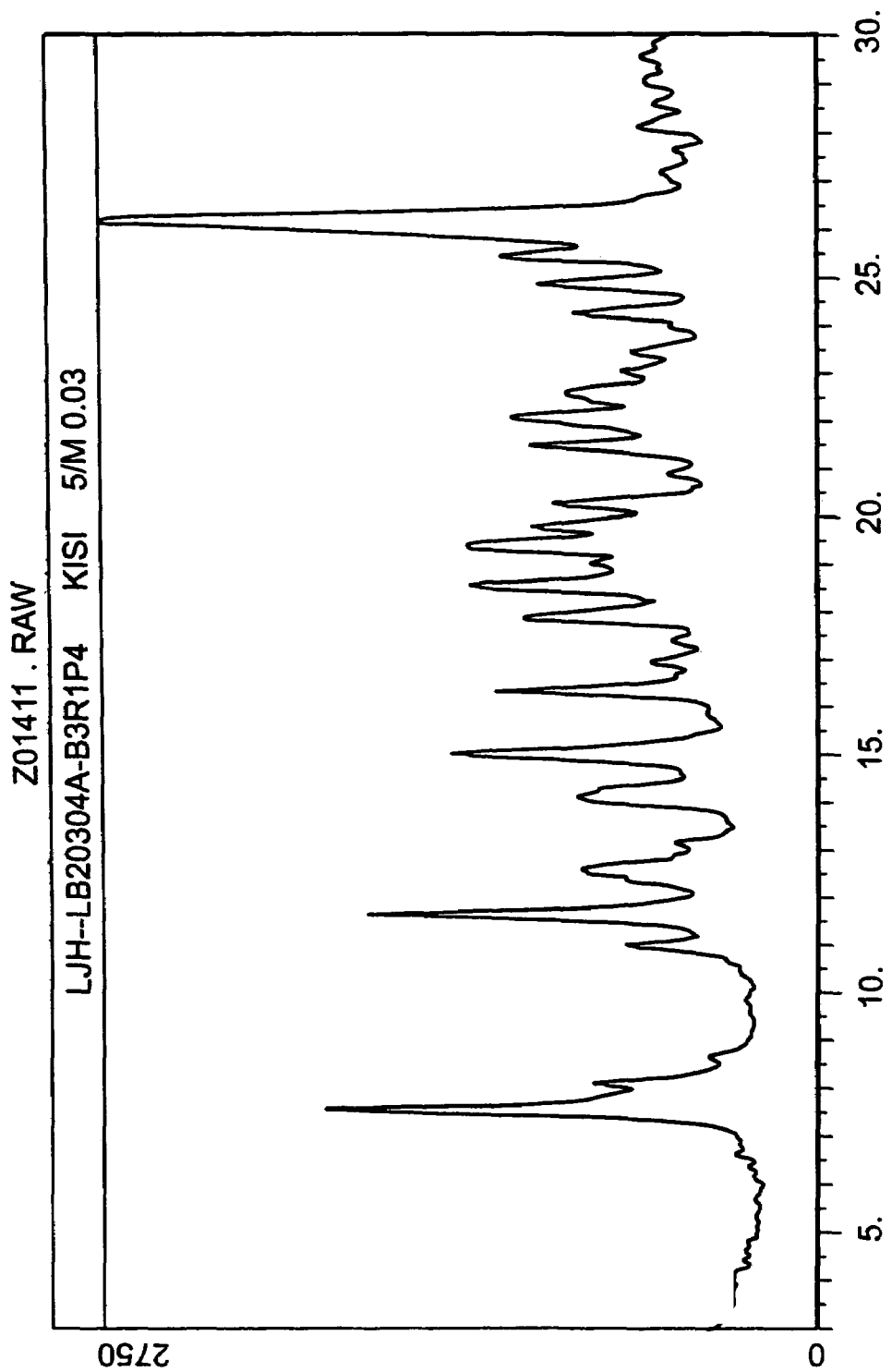
FIG. 6 shows the powder X-ray diffraction pattern of the methanesulfonate n=3 hydrate of Example 2. The characteristic peaks are $2\theta=7.7, 11.8°$. The exact position of peaks can vary slightly depending on the experimental conditions.
Figure 7:
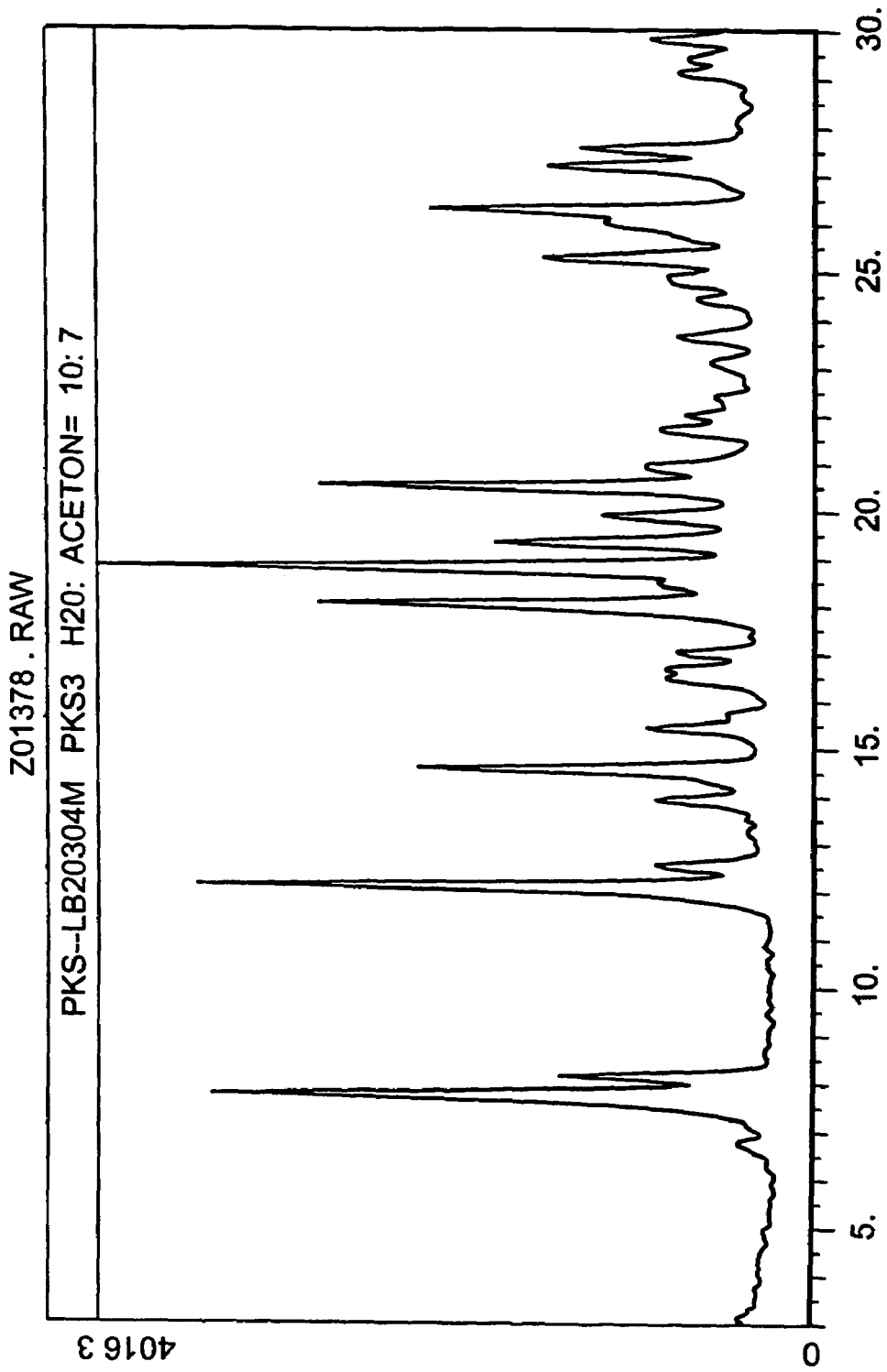
FIG. 7 shows the powder X-ray diffraction pattern of the methanesulfonate n=1.5. hydrate of Example 3. The characteristic peaks are $2\theta=8.0, 12.2, 14.7°$. The exact position of peaks can vary slightly depending on the experimental conditions.
Figure 9:
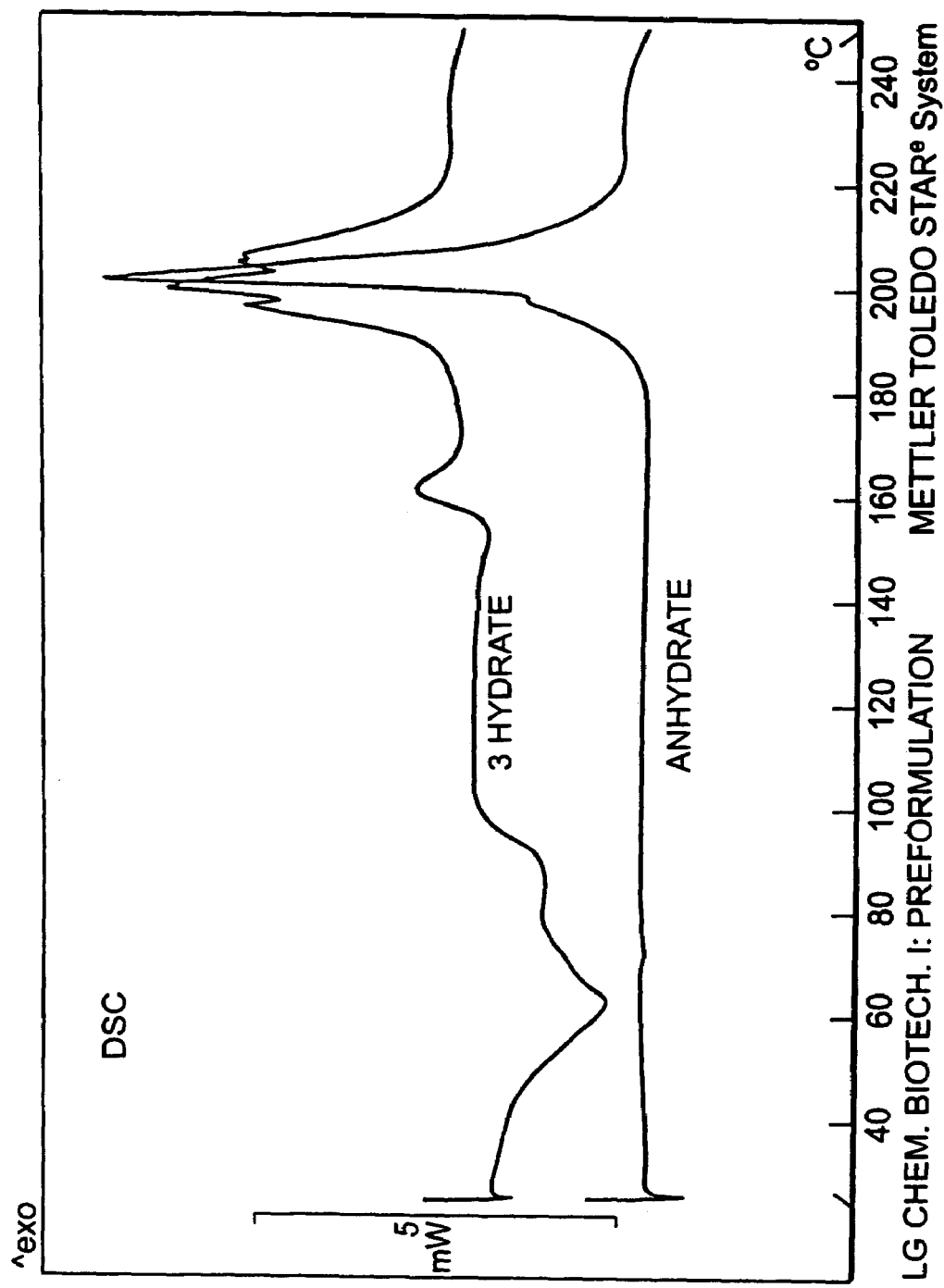
FIG. 9 shows the Differential Scanning Calorimetry on the methanesulfonate anhydrate of Example 1 and the methanesulfonate n=3 hydrate of Example 2.
Figure 10:
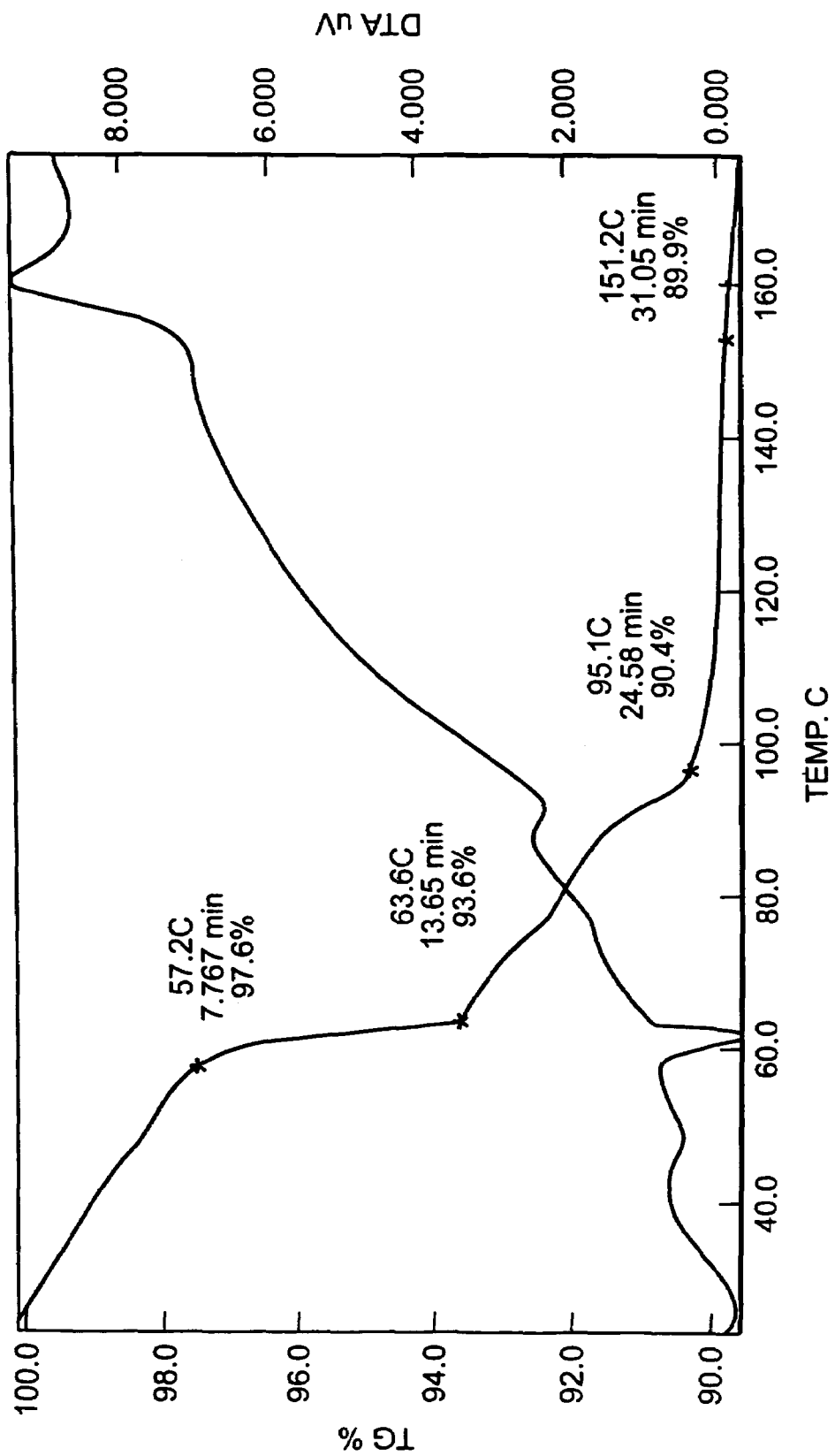
FIG. 10 shows the results of thermogravimetric analysis on the methanesulfonate n=3 hydrate of Example 2.

For example, by comparing the powder X-ray diffraction patterns of the anhydrate in FIG. 5, the n=3 hydrate in FIG. 6, and the n=1.5 hydrate in FIG. 7, it can be seen that their crystal forms are different from each other. In addition, the thermal analysis using Differential Scanning Calorimetry (DSC) shows that the endothermic peak produced by the vaporization of the water molecules contained in the n=3 hydrate begins at around 50° C. and the exothermic peak by thermal decomposition is observed at around 185 to 220° C., whereas the anhydrate shows only an exothermic peak at around 185 to 220° C. due to the thermal decomposition without any endothermic peak (see, FIG. 9). At the same time, the thermogravimetric analysis shows a weight decrement at the temperature range of endothermic peak, the extent of which corresponds to the moisture content quantified by Karl-Fisher method (Mettler Toledo DL37KF Coulometer)(see, FIG. 10). Therefore, it is verified that the endothermic peak shown in the DSC analysis is due to the evaporation of a water molecule.

The present inventors also compared the chemical stability under heating of the hydrates with that of the anhydrate in order to identify the influence of hydration on the chemical stability. In this test, the anhydrate and hydrate were each kept at 70° C. for 4 weeks, and the extent of decomposition is analyzed by liquid chromatography. No difference in the extent of decomposition was noticed between the hydrates and the anhydrate, and thus confirming that the hydrate has the same chemical stability as the anhydrate.

The methanesulfonate anhydrate or a solvate thereof may be converted into a hydrate under appropriate conditions as described above. This process can be monitored by the change in the X-ray diffraction pattern of the compound and the decrease in the amount of organic solvent in the compound. Such changes being caused by the water molecules newly intercalated into the crystal structure.

Figure 11:
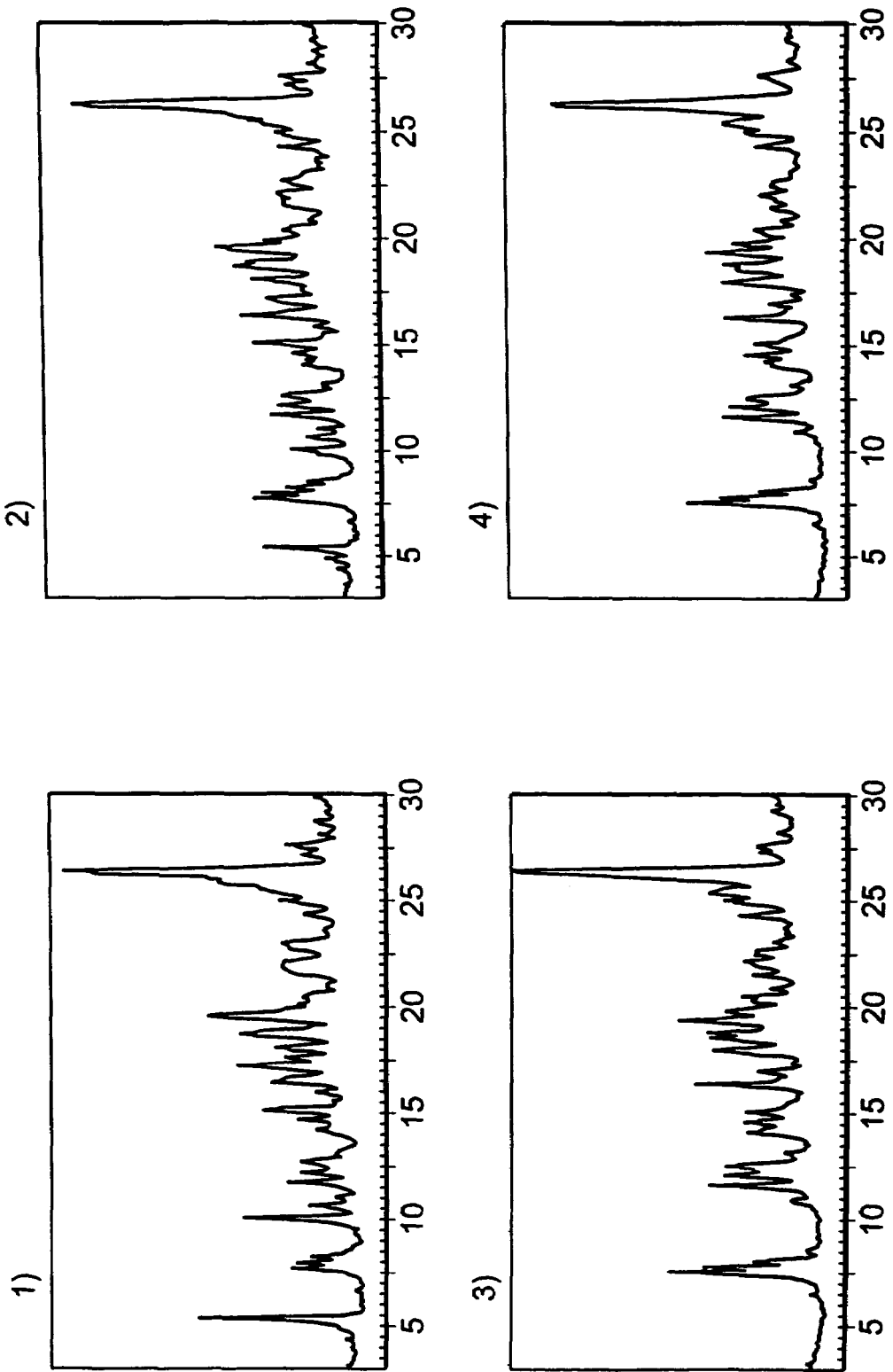
Figure 12:
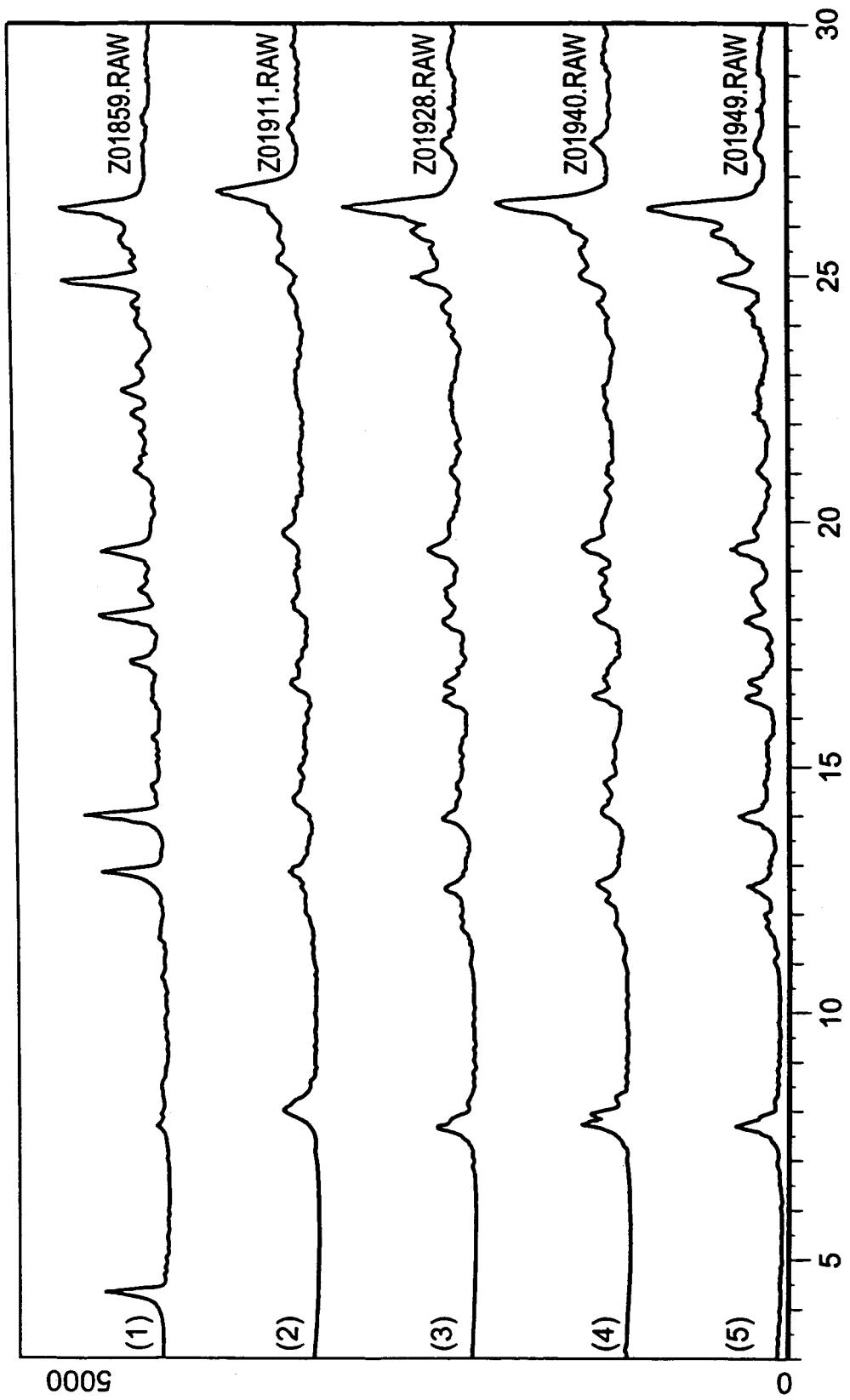
FIG. 12 shows the change in X-ray diffraction pattern with elapsed time of the methanesulfonate solvate (ethanol content 1.9%) of Example 5, from the initial point of standing the sample under a relative humidity of 93%.

As can be seen from FIG. 11, the X-ray diffraction peaks based on the solvate disappear with the passing of humidified nitrogen gas to leave the peaks based on the hydrate. This shows that all the solvates is converted into hydrates. The residual solvent is decreased to the amount of less than the quantitative limit simultaneously with the change of X-ray diffraction. FIG. 12 shows that the X-ray diffraction peaks based on the solvate disappear when the solvate is allowed to stand under a relative humidity of 93%. However, there is no change in the X-ray diffraction pattern when the solvate is allowed to stand under a relative humidity of 11% or 52% (see FIG. 13). Therefore, it is recognized that the change shown in FIG. 12 occurs not by the spontaneous evaporation of the residual solvent but by the substitution of the organic solvents in the crystal by water molecules.

In preparing the hydrate according to the processes described above, the respective hydrates having a different hydration number can be obtained by changing conditions such as humidity, time, temperature, etc. or by changing the recrystallization condition. Such conditions should be adjusted according to whether the starting material is the anhydrate or a solvate, and depending on the nature of the solvate.

The present invention will be more specifically explained by the following examples and experimental examples. However, it should be understood that the examples are intended to illustrate but not in any manner limit the scope of the present invention.

EXAMPLE 1

Synthesis of 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate anhydrate 7-(3-Aminomethyl-4-methyloxyiminopyrrolidin-1-yl)-1-cyclopropyl-6-fluoro-4-oxo-1,4-dihydro-1,8-naphthyridine-3-carboxylic acid (3.89 g, 10 mmol) was suspended in a mixture of dichloromethane and ethanol (110 ml, 8:2 v/v). Methanesulfonic acid (0.94 g, 9.8 mmol) was added dropwise and the resulting solution was stirred for 1 hour at 0° C. The resulting solid was filtered, washed with ethanol then dried to give the title compound (4.55 g).

m.p.: 195° C. (dec.) $^1$H NMR(DMSO-$d_6$) δ (ppm): 8.57 (1H, s), 8.02(1H, d), 7.98(3H, br), 4.58(2H, br), 4.39(1H, m), 3.91(3H, s), 3.85(1H, m), 3.71(1H, m), 3.42(1H, m), 3.20~3.10(2H, m), 1.20~1.10(4H, m)

EXAMPLE 2

Figure 8:
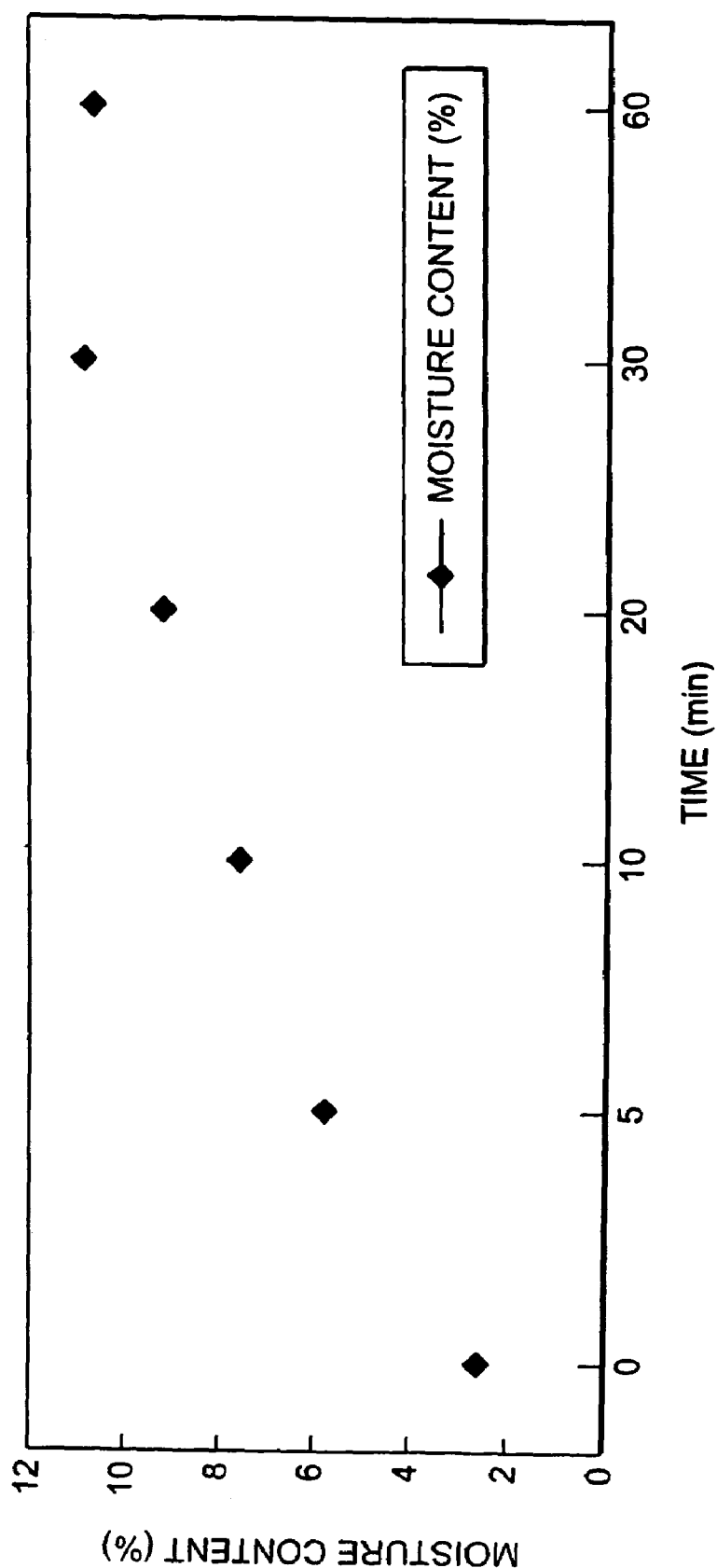

Synthesis of 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate n=3 hydrate A sonicator filled with water was adjusted to 40° C., sealed with a lid and a nitrogen inlet and outlet connected. When the pressure of the dried nitrogen introduced through the inlet was 20 psi the relative humidity of the nitrogen exiting through the outlet was more than 93%. The anhydrate of Example 1 having a moisture content of 2.5% (1.0 g) was introduced into a fritted filter and the humidified nitrogen produced as described above passed through the filter. Samples were taken after 0, 5, 10, 20, 30, and 60 minutes and the moisture content measured. From the results shown in FIG. 8 it can be seen that a moisture content of about 10% is maintained when the humidifying procedure is carried out over about 30 minutes. The X-ray diffraction pattern of the humidified sample was identical to that of the n=3 hydrate obtained by recrystallization.

EXAMPLE 3

Synthesis of 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate n=1.5 hydrate The title compound was prepared by the following routes:
Route A
The anhydrate of Example 1 (1.0 g) was dissolved in a mixture of water and acetone (17 ml, 10:7 v/v). The solvent was slowly evaporated in darkness leaving the title compound as a solid (0.8 g).
Route B
The anhydrate of Example 1 (5.0 g) was added to water (10 ml) and the mixture was heated to 45° C. to aid dissolution. Ethanol (20 ml) was added and the resulting solution stirred then allowed to stand. The resulting solid was filtered and dried under a flow of nitrogen to give the title compound (2.6 g).

EXAMPLE 4

Synthesis of the hydrate from 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate solvate using a humidified nitrogen gas A sonicator filled with water was adjusted to 40° C. and was sealed with a lid. Then, a nitrogen inlet and outlet were connected to the vessel. When the pressure of the dried nitrogen introduced through the nitrogen inlet was adjusted to about 20 psi, the relative humidity of the humidified nitrogen gas exiting through the outlet was more than 93%. The solvate (1 g, ethanol 0.11%) of the anhydrate of Example 1 was introduced into a fritted filter and the humidified nitrogen gas prepared as described above was passed through the filter. Samples were taken after 40 minutes, 3.5 and 6 hours, respectively. The change in the amount of residual organic solvent and X-ray diffraction pattern with the lapse of time were examined. After 3.5 hours, it was identified that the product contained the organic solvent in an amount of less than 50 ppm and that the peaks based on the solvate disappeared, whilst the peaks based on the mixture of n=3 hydrate and n=1.5 hydrate appeared.

EXAMPLE 5

Synthesis of the hydrate from 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate solvate using a high relative humidity Saturated aqueous potassium nitrate solution was placed in a desiccator, and accordingly the relative humidity inside the desiccator was controlled to 93%. For tests under relative humidity of 11% or 52%, desiccators containing saturated aqueous solutions of lithium chloride and magnesium nitrate, respectively, were prepared. Into the desiccator having a relative humidity of 93% was introduced a solvate(1.9% ethanol) of the anhydrate of Example 1, and into each of the desiccators having a relative humidity of 93%, 52% or 11% was introduced a solvate (0.12% ethanol) of the anhydrate of Example 1. The solvates were stored so as not to directly contact the aforementioned salt solutions. After a certain period of time has passed, samples were taken and subjected to gas chromatography in order to analyze the residual solvent. As a result, it was identified that solvates stored for 4 weeks under a relative humidity of 93% contained the organic solvent in an amount of less than 50 ppm. Also, it was identified by X-ray diffraction pattern that peaks based on the solvates disappeared after 4 weeks. To the contrary, in the case where the samples were stored under a relative humidity of 52% or 11%, the amount of residual organic solvent and X-ray diffraction pattern after 4 weeks were identical with those at the beginning.

EXAMPLE 6

Synthesis of n=3 hydrates from 7-(3-amino-methyl-4-methoxyiminopyrrolidin-1-yl)-1-cyclopropyl-6-fluoro-4-oxo-1,4-dihydro-1,8-naphthyridine-3-carboxylic acid methanesulfonate solvates Dried nitrogen gas and humidified nitrogen gas having a relative humidity of 78 to 84% were passed over 24 hours, respectively, through log of four different solvates each of which had a different kind and amount of organic solvent from the others. The amount of residual organic solvent was measured and the change in X-ray diffraction pattern was analyzed, the results of which are shown in Table 2. The X-ray diffraction analysis shows that the samples through which dried nitrogen gas was passed remained as the original solvates, while the samples through which humidified nitrogen gas was passed had the same X-ray diffraction pattern and crystallinity as those of the n=3 hydrate obtained by recrystallization.

The results from this Example suggests that water molecules contained in the humidified nitrogen gas replace the organic solvents in the solvate. This suggestion is also supported by the change in X-ray diffraction pattern influenced by a relative humidity.

TABLE 2

| Sample No. | The kind and amount of the residual organic solvent after dried nitrogen gas has passed for 24 hours | The kind and amount of the residual organic solvent after humidified nitrogen gas (78~84% RH) has passed for 24 hours |
| --- | --- | --- |
| 1 | Methylene chloride 1.14%, Ethanol 3.73% | 0.08% <50 ppm |
| 2 | Isopropanol 0.45% | 0.06% |
| 3 | 2-Isopropanol 0.24% | 0.04% |
| 4 | 2-Methyl-2-propanol 0.07% Ethanol 0.06% | 0.01% <50 ppm |

EXAMPLE 7

Synthesis of the ethanolate containing ethanol 0.11%

The anhydrate of Example 1 (5.0 g) was added to a solvent mixture of ethanol (25 ml) and water (25 ml) and the mixture was heated to 50° C. to facilitate dissolution. Then, the solution was cooled slowly to −3° C. and allowed to stand at that temperature for about 3 hours. The resulting solid was filtered and washed with a solvent mixture of ethanol and water (16.5 ml, ethanol:water=20:8, v/v) to give the title compound quantitatively.

TEST EXAMPLE 1

Moisture Sorption of the Anhydrate of Example 1

The moisture sorption velocity and the equilibrium moisture content of the anhydrate of Example 1 was determined by means of an automatic moisture sorption analyzer (MB 300G Gravimetric Sorption Analyzer). This instrument produces a specific relative humidity at a specific temperature and continuously records the weight change of a sample due to adsorption or desorption of moisture as measured by a micro balance inside the instrument. The anhydrate of Example 1 (16 mg) was loaded onto the micro balance and the moisture contained in the sample removed under a stream of dried nitrogen at 50° C. A weight change of less than 5 µg per 5 minutes was the criterion for complete dryness. Thereafter, the inner temperature was adjusted to 25° C. and the sample tested at 5% intervals whilst varying the humidity from 0 to 95%. The sample was considered to have reached equilibrium when the weight change was less than 5 µg per 5 minutes. FIG. 1 shows the moisture adsorption velocity, that is the time required for the sample to reach equilibrium at each relative humidity. As can be seen initial moisture adsorption proceeded rapidly at each relative humidity tested, in most cases equilibrium was reached within 2 hours. FIG. 2 shows the weight increment at each relative humidity, i.e. the equilibrium moisture content. It is clear from FIG. 2 that the equilibrium moisture content of the anhydrate is dependent on the relative humidity.

TEST EXAMPLE 2

Thermal Analysis of the Anhydrate of Example 1 and n=3 hydrate of Example 2

For the Differential Scanning Calorimetry, METTLER TOLEDO DSC821e and METTLER TOLEDO STARe System were used. The sample (3.7 mg) was weighed into the aluminum pan which was then press sealed with an aluminum lid. Three tiny needle holes were made on the lid and the sample tested by heating from normal temperature to 250° C. at a rate of 10° C./min. As can be seen from FIG. 9, the endothermic peak due to the vaporization of the water molecules contained in the n=3 hydrate begins at around 50° C. and the exothermic peak due to the thermal decomposition is observed at around 180 to 220° C. In contrast, the anhydrate showed only an exothermic peak due to the thermal decomposition at around 185 to 220° C. without any endothermic peak.

In the thermogravimetric analysis, SEIKO TG/DTA220 was used. The sample (3.8 mg) was weighed into an aluminum pan and was heated from normal temperature to 250° C. at a rate of 10° C./min according to the temperature raising program. As can be seen from FIG. 10, weight decrement was observed at the temperature range of endothermic peak, the extent of which corresponds to the moisture content determined by Karl-Fisher method (Mettler Toledo DL37KF Coulometer).

TEST EXAMPLE 3

Equilibrium Moisture Content Determination of Hydrates

Six saturated aqueous salt solutions were introduced into each desiccator to control the inner relative humidity to a specific value as shown in Table 3. Then, equilibrium moisture contents of n=3 hydrate and n=1.5 hydrate of Examples 2 and 3, respectively, were determined at several relative humidities.

TABLE 3

| Saturated salt solutions, inside the desiccator | |
|---|---|
| Salt Solution | Relative Humidity (%) at 25° C. |
| Potassium Acetate | 23 |
| Magnesium Chloride | 33 |
| Potassium Carbonate | 43 |
| Magnesium Nitrate | 52 |
| Sodium Nitrite | 64 |
| Sodium Chloride | 75 |

The sample (100 mg) was spread on a pre-weighed Petri dish and the total weight was accurately measured, then three of the sample were placed in each desiccator of Table 3. The desiccators were allowed to stand at normal temperature for 7 days and then the sample was taken to be weighed. After 13 days, one of the three samples inside each desiccator was taken and the moisture content of each was measured by the thermogravimetric analysis described in Test Example 2. Equilibrium moisture content at each relative humidity is represented in FIG. 3 (n=3 hydrate) and FIG. 4 (n=1.5 hydrate). FIG. 3 shows that moisture content of the n-3 hydrate is maintained around 10% for the whole relative humidity range tested; FIG. 4 shows that the moisture content of the n=1.5 hydrate is maintained around 5% at the relative humidity of 23 to 64%. Both hydrates are stable since they maintain a constant equilibrium moisture content regardless of the relative humidity change.

TEST EXAMPLE 4

X-ray Diffraction Analysis

The anhydrate of Example 1, n=3 hydrate of Example 2 and n=1.5 hydrate of Example 3 (50mg of each) were thinly spread on the sample holder, X-ray diffraction analysis (35 kV×20 mA Rigaku Gergeflex D/max-III C) were performed under the conditions listed below.
  scan speed (2θ) 5°/min
  sampling time: 0.03 sec
  scan mode: continuous
  2θ/θ reflection
  Cu-target (Ni filter)
Results of X-ray diffraction analyses on the anhydrate, n=3 hydrate, and the n=1.5 hydrate are shown in FIG. 5, 6, and 7. The diffraction patterns illustrate the difference in crystal form of these 3 compounds.

According to a further aspect of the invention we provide 7-(3-aminomethyl-4-methoxyiminopyrrolidin-1-yl)-1-cyclopropyl-6-fluoro-4-oxo-1,4-dihydro-1,8-naphthyridine-3- carboxylic acid methanesulfonate having an X-ray diffraction pattern substantially as shown in FIG. 5, 6 or 7.

We also provide 7-(3-aminomethyl-4-methoxyiminopyrrolidin-1-yl)-1-cyclopropyl-6-fluoro-4-oxo-1,4-dihidro-1,8-naphthyridine-3-carboxylic acid methanesulfonate hydrate having peaks at 2θ=8.0, 12.2 and 14.7° in its X-ray diffraction pattern; and 7-(3-aminomethyl-4-methoxy-iminopyrrolidin-1-yl)-1-cyclopropyl-6-fluoro-4-oxo-1,4-dihydro-1,8-n aphthyridine-3-carboxylic acid methanesulfonate hydrate having peaks at 2θ=7.7 and 11.8° in its X-ray diffraction pattern.

Figure 13:
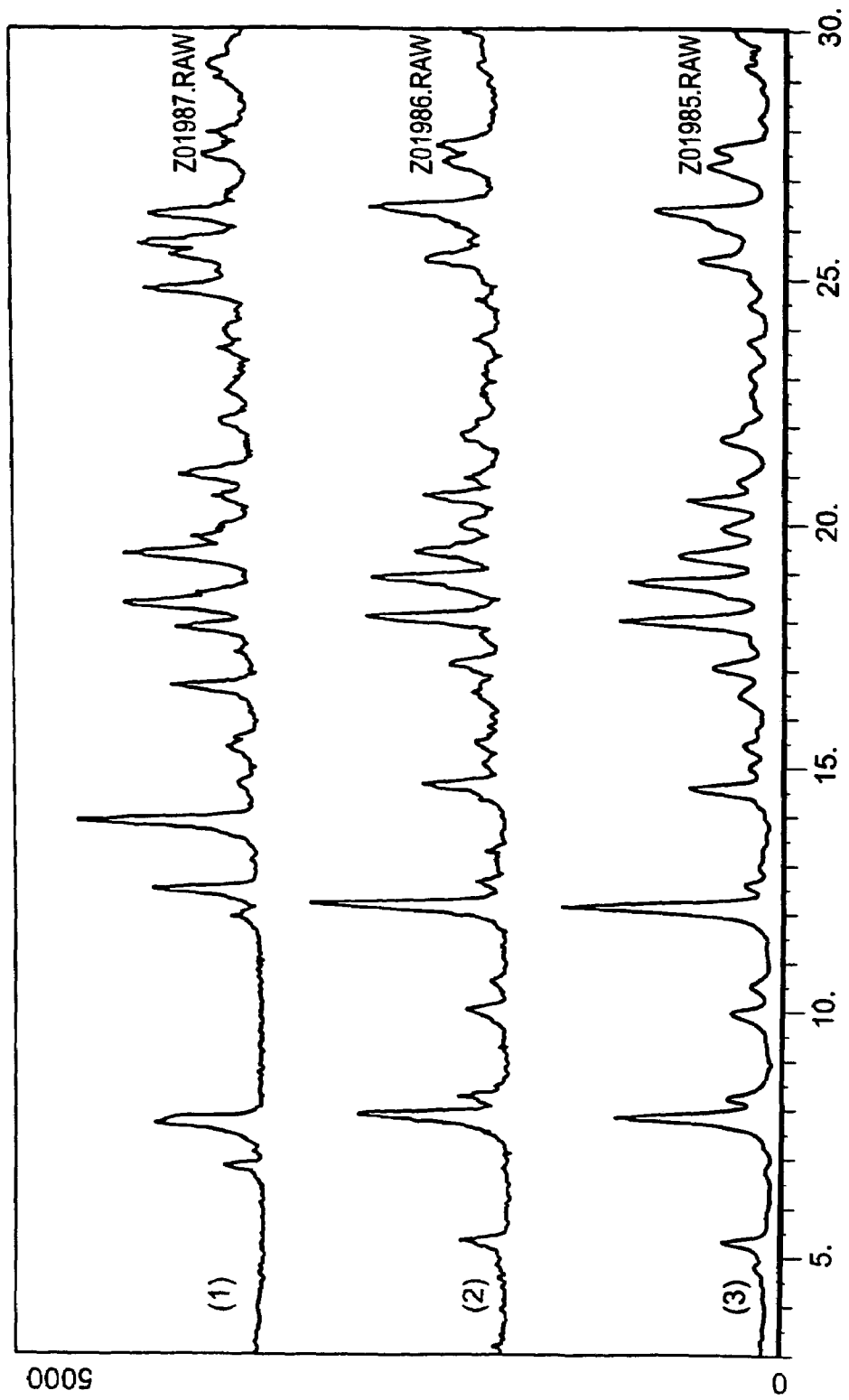
FIG. 13 shows the change in X-ray diffraction pattern of the methanesulfonate solvate (ethanol content 0.12%) of Example 5 under various relative humidities, that is, relative humidity of 93% (1), relative humidity of 52% (2) and relative humidity of 11% (3), respectively.

The change of crystallinity during the conversion from the solvate to the hydrate in Examples 4 and 5 was identified by X-ray diffraction analysis under the same conditions as mentioned above (see, FIG. 11 to 13). FIG. 11 shows the X-ray diffraction pattern of the solvate is changed into that of the n=3 hydrate (see, Example 4);. FIG. 12 represents the change in X-ray diffraction pattern of the solvate containing 1.9% of ethanol before and after storage of one week, two weeks, three weeks and four weeks at 93% of relative humidity; and FIG. 13 represents the change in X-ray diffraction pattern of the solvate containing 0.12% of ethanol after storage of four weeks at 93%, 52% and 11% of relative humidity, respectively (see, Example 5).

TEST EXAMPLE 5

Chemical Stability

The chemical stability of the n=3 hydrate of Example 2 and the n=1.5 hydrate of Example 3 and the anhydrate of Example 1 were compared at elevated temperature in order to determine the effect on chemical stability of the extent of hydration.

The anhydrate and each of the hydrates were introduced into a glass vial and maintained at 70° C. The extent of decomposition with elapsed time was analyzed by liquid chromatography. The results obtained are shown in Table 4.

TABLE 4

Thermal stability with elapsed time (at 70° C., Unit: %)

| Sample | Initial | Time (week) | | | |
|---|---|---|---|---|---|
| | | 1 | 2 | 3 | 4 |
| Anhydrate | 100 | 99.8 | 98.6 | 97.7 | 96.7 |
| n = 3 hydrate | 100 | 102.4 | 100.7 | 99.2 | 99.2 |
| n = 1.5 hydrate | 100 | 97.3 | 95.8 | 97.2 | 96.2 |

As can be seen from Table 4, the n=3 hydrate and the n=1.5 hydrate both show the same degree of chemical stability as the anhydrate.

TEST EXAMPLE 6

In vitro Antibacterial Activity

In order to determine whether 7-(3-aminomethyl-4-methyloxyimino-pyrrolidin-1-yl)-1-cyclopropyl-6-fluoro-4-oxo-1, 4-dihydro-1,8-naphthyridine-3-carboxylic acid methanesulfonate has the same antibacterial activity as the free base, in vitro antibacterial activity of the methanesulfonate was measured using agar medium dilution method. The results are shown in Tables 5. The minimum inhibitory concentration (MIC, μg/ml) was simply calculated in the ratio of weight without considering the molecular weight, and ciprofloxacin was chosen as the control.

TABLE 5

In vitro Antibacterial activity (Minimum Inhibitory Concentration: MIC, μg/ml)

| Test Strains | Methanesulfonic acid salt | Ciprofloxacin |
|---|---|---|
| Staphylococcus aureus 6538p | 0.016 | 0.13 |
| Staphylococcus aureus giorgio | 0.016 | 0.13 |
| Staphylococcus aureus 77 | 0.031 | 0.25 |
| Staphylococcus aureus 241 | 4 | 128 |
| Staphylococcus aureus epidermidis 887E | 0.016 | 0.13 |
| Staphylococcus aureus epidermidis 178 | 4 | 128 |
| Staphylococcus aureus faecalis 29212 | 0.13 | 0.5 |
| Bacillus subtilis 6633 | 0.016 | 0.031 |
| Micrococcus luteus 9431 | 0.13 | 2 |
| Escherichia coli 10536 | 0.008 | <0.008 |
| Escherichia coli 3190Y | 0.008 | <0.008 |
| Escherichia coli 851E | 0.016 | <0.008 |
| Escherichia coli TEM3 3455E | 0.25 | 0.5 |
| Escherichia coli TEM5 3739E | 0.13 | 0.13 |
| Escherichia coli TEM9 2639E | 0.031 | 0.016 |
| Pseudomonas aeruginosa 1912E | 0.25 | 0.13 |
| Pseudomonas aeruginosa 10145 | 0.5 | 0.5 |
| Acinetobacter calcoaceticus 15473 | 0.031 | 0.25 |
| Citrobacter diversus 2046E | 0.031 | 0.016 |
| Enterobacter cloacae 1194E | 0.031 | 0.016 |
| Enterobacter cloacae P99 | 0.016 | <0.008 |
| Klebsiella aerogenes 1976E | 0.13 | 0.13 |
| Klebsiella aerogenes 1082E | 0.031 | 0.016 |
| Proteus vulgaris 6059 | 0.25 | 0.031 |
| Seratia marsecence 1826E | 0.13 | 0.063 |
| Salmonella thypimurium 14028 | 0.031 | 0.031 |

TEST EXAMPLE 7

Water Solubility of the Anhydrate of Example 1

The water solubility of the free base and various salts of 7-(3-aminomethyl-4-methoxyiminopyrrolidin-1-yl)-1-cyclopropyl-6-fluoro-4-oxo-1,4-dihydro-1,8-naphthyridine-3-carboxylic acid, including the methanesulfonate of Example 1, was measured at 25° C. The results are shown in Table 6.

TABLE 6

Water Solubility (at 25° C.)

| Sample | Solubility in water (mg/ml) |
|---|---|
| Free form | 0.007 |
| Tartrate | 6.7 |
| Sulfurate | 11.4 |
| p-Toluenesulfonate | 7.5 |
| Methanesulfonate | >30 |

As can be seen, the methanesulfonate shows increased water solubility compared to that of the tartrate, the sulfurate, and the p-toluenesulfonate and the free base.

What is claimed is:

1. A method of treating a respiratory tract infection in a human or animal, comprising administering a therapeutically effective amount of a composition comprising 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate hydrate and a pharmaceutically acceptable carrier or excipient to a human or animal with a respiratory tract infection.

2. A method of treating a urinary tract infection in a human or animal, comprising administering a therapeutically effective amount of a composition comprising 7-(3-aminomethyl-4-methoxyiminopyrrolidin-1-yl)-1-cyclopropyl-6-fluoro-4-oxo-1,4-dihydro-1,8-naphthyridine-3-carboxylic acid methanesulfonate hydrate and a pharmaceutically acceptable carrier or excipient to a human or animal with a urinary tract infection.

3. The method of claim 1, wherein the hydration number of the methanesulfonate hydrate is 1.5.

4. The method of claim 1, wherein the hydration number of the methanesulfonate hydrate is 3.0.

5. The method of claim 2, wherein the hydration number of the methanesulfonate hydrate is 1.5.

6. The method of claim 2, wherein the hydration number of the methanesulfonate hydrate is 3.0.

* * * * *